(12) United States Patent
Egi et al.

(10) Patent No.: US 6,288,113 B1
(45) Date of Patent: Sep. 11, 2001

(54) ANGIOGENESIS PROMOTERS

(75) Inventors: Yasuhiro Egi; Yoshiji Kubo, both of Hirakata; Satoru Inoue, Osaka; Hideaki Kido; Masakuni Nishikawa, both of Fukuoka; Kazutaka Hayashi, Hirakata, all of (JP)

(73) Assignees: Welfide Corporation, Osaka; Yutaka Mizushima, Tokyo; Seikagaku Corporation, Tokyo, all of (JP)

( * ) Notice: Subject to any disclaimer, the term of this patent is extended or adjusted under 35 U.S.C. 154(b) by 0 days.

(21) Appl. No.: 09/486,312

(22) PCT Filed: Aug. 24, 1998

(86) PCT No.: PCT/JP98/03754
§ 371 Date: Jun. 21, 2000
§ 102(e) Date: Jun. 21, 2000

(87) PCT Pub. No.: WO99/09992
PCT Pub. Date: Mar. 4, 1999

(30) Foreign Application Priority Data

Aug. 27, 1997 (JP) .................................. 9-231110

(51) Int. Cl.$^7$ ................................................. A61K 31/215
(52) U.S. Cl. ................................................. 514/530; 424/317
(58) Field of Search ............................. 514/530; 424/317

(56) References Cited

U.S. PATENT DOCUMENTS

| | | | |
|---|---|---|---|
| 4,363,817 | 12/1982 | Biddlecom | 424/311 |
| 4,493,847 | 1/1985 | Mizushima et al. | 424/317 |
| 4,543,421 | 9/1985 | Corey et al. | 560/106 |
| 4,684,633 | 8/1987 | Imagawa et al. | 514/78 |
| 5,120,870 | 6/1992 | Mizushima et al. | 560/121 |
| 5,194,670 | 3/1993 | Mizushima et al. | 560/121 |
| 5,767,079 | * 6/1998 | Glaser et al. | 514/12 |

FOREIGN PATENT DOCUMENTS

| | | |
|---|---|---|
| 3-204853 | 9/1991 | (JP) . |
| 5-213862 | 8/1993 | (JP) . |

OTHER PUBLICATIONS

M. Ziche et al., "Angiogenesis can be stimulated or repressed in vivo by a change in GM3:GD3 ganglioside", Laboratory Investigation, vol. 67, No. 6, 1992, pp. 711–715.

M. Ziche et al., "Ganglioside promote the angiogenic response", Laboratory Investigation, vol. 61, No. 6, 1989, pp. 629–634.

M. Ziche et al., "Gangliosides Promote the Angiogenic Response", Laboratory Investigation, vol. 61, No. 6, pp. 629–634.

M. Ziche et al., "Angiogenesis can be Stimulated or Repressed in vivo by a change in GM3:GD3 Ganglioside Ratio", Laboratory Investigation, vol. 67, No. 6, pp. 711–715.

* cited by examiner

Primary Examiner—James H. Reamer
(74) Attorney, Agent, or Firm—Wenderoth, Lind & Ponack, L.L.P.

(57) ABSTRACT

An angiogenesis promoter containing a compound of the following formula (I)

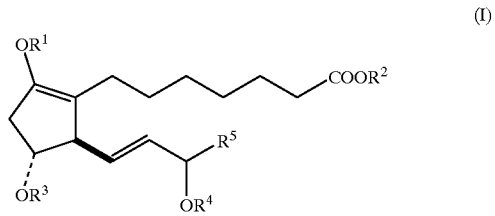

wherein $R^1$ is acyl, $R^2$ is alkyl, $R^3$ and $R^4$ are the same or different and each is hydrogen atom or hydroxy protecting group and $R^5$ is alkyl, as an active ingredient. This compound itself not only has an angiogenesis promoting effect but also potentiates the angiogenic effect by a drug (e.g., b-FGF) having such effect. Therefore, it can express the angiogenesis promoting effect more effectively in the ischemic tissues and the site under different disease state, where b-FGF has locally increased.

18 Claims, 3 Drawing Sheets

ANGIOGENESIS PROMOTERS

This Application is a 371 of PCT/JP98/03754 filed Aug. 24, 1998.

TECHNICAL FIELD

The present invention relates to a new use of a prostaglandin $E_1$ precursor. More specifically, the present invention relates to an angiogenesis promoter and a potentiator of an angiogenic effect due to a growth factor.

BACKGROUND ART

It is known that prostaglandin $E_1$ ($PGE_1$) exists in a trace amount in a living body, has a broad range of physiological actions and the like, but lacks chemical stability. Therefore, an improvement in the formulation of a preparation and modification of $PGE_1$ have been considered. In particular, a $PGE_1$ precursor (prodrug) has been drawing attention. It is therefore an object of the present invention to provide a new use of a $PGE_1$ precursor.

DISCLOSURE OF THE INVENTION

The present inventors have found that a specific $PGE_1$ precursor has an angiogenesis promoting effect and potentiates the angiogenic effect by a growth factor, such as basic fibloblast growth factor (hereinafter to be referred to as b-FGF), which resulted in the completion of the present invention.

Accordingly, the present invention provides an angiogenesis promoter comprising a compound of the following formula (I)

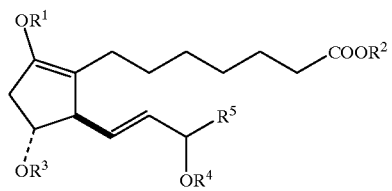

wherein $R^1$ is acyl, $R^2$ is alkyl, $R^3$ and $R^4$ are the same or different and each is hydrogen atom or hydroxy protecting group and $R^5$ is alkyl (hereinafter to be also referred to PGE$_1$ precursor), as an active ingredient. The present invention also provides a potentiator of an angiogenic effect of a drug having such effect, which contains a $PGE_1$ precursor as an active ingredient.

The acyl at $R^1$ of the formula (I) has 2 to 6, preferably 2 to 4, carbon atoms. Preferable examples thereof include alkanoyl such as acetyl, propionyl, butyryl, pivaloyl, hexanoyl and the like. The alkyl at $R^2$ has 1 to 30, preferably 1 to 4, carbon atoms. Examples thereof include methyl, ethyl, propyl, butyl, hexyl, octyl, decyl, icosyl, triacosyl and the like. The alkyl at $R^5$ has 1 to 10, preferably 5 to 7, carbon atoms. Examples thereof include the above-mentioned alkyl having the corresponding carbon atoms and the like. The hydroxy protecting group at $R^3$ and $R^4$ includes, for example, acyl (e.g., acetyl, propionyl, benzoyl and the like), aralkyl (e.g., benzyl, phenylethyl and the like), and the like.

Specific examples of the $PGE_1$ precursor of the formula (I) include methyl 9-acetoxy-11α,15S-dihydroxyprosta-8,13E-dien-1-oate, methyl 9,11α,15S-triacetoxyprosta-8,13E-dien-1-oate, methyl 9,15R-diacetoxy-11α-hydroxyprosta-8,13E-dien-1-oate, methyl 9,15S-diacetoxy-11α-hydroxyprosta-8,13E-dien-1-oate, butyl 9-acetoxy-11α,15S-dihydroxy-17S,20-dimethylprosta-8,13E-dien-1-oate, butyl 9-acetoxy-11α,15S-dihydroxyprosta-8,13E-dien-1-oate, butyl 9-butyryloxy-11α,15S-dihydroxyprosta-8,13E-dien-1-oate, butyl 9,11α-diacetoxy-15S-hydroxy-17S,20-dimethylprosta-8,13E-dien-1-oate and the like.

The methods for preparing the compounds of the formula (I) are disclosed in JP-A-58-39660 (corresponding U.S. Pat. No. 4,363,817, U.S. Pat. No. 4,543,421, EP-A-133450), JP-A-3-204853 (corresponding U.S. Pat. No. 5,120,870, EP-A-423697), JP-A-5-213862 (corresponding USP 5194670, EP-A-624574) and the like.

The $PGE_1$ precursor can be used upon preparation into a suitable dosage form by inclusion in cyclodextrin (CD), formulating into a liposome, preparing into an ethanol solution, preparing into a lipid emulsion and the like. Preferred is the form of a lipid emulsion which is superior in sustained release, duration, local cumulativeness and stability during storage.

The preferable form of lipid emulsion is explained in the following. In the present invention, a lipid emulsion containing a $PGE_1$ precursor (hereinafter to be also referred to as $PGE_1$ precursor-containing lipid emulsion) is a preparation containing a $PGE_1$ precursor and an oil component dispersed in a dispersing medium as liquid drops.

The oil component is exemplified by vegetable oil, middle chain fatty acid triglyceride (so-called MCT), fish oil and the like. These may be used alone or in combination. Examples of the vegetable oil include soybean oil, sesame oil, castor oil, cottonseed oil, olive oil and the like. These need only purified by a known method to a level permitting clinically safe use. Preferred is purified soybean oil having high purity, more preferably purified soybean oil having high purity (purity: containing 99.9% or above as triglyceride, diglyceride and monoglyceride) obtained by further purifying the purified soybean oil by, for example, steam distillation method.

To disperse the oil component in a dispersing medium, phospholipid and the like are used as emulsifiers. Examples of the phospholipid include egg yolk phospholipid, soybean phospholipid and the like, and purified phospholipids thereof are particularly preferably used. The purified phospholipid can be prepared by a conventional method using fractionation with an organic solvent. The purified phospholipid mainly consists of phosphatidylcholine, phosphatidylethanolamine, and, as a phospholipid other than these, phosphatidylinositol, phosphatidylserine, sphingomyelin and the like. In addition, a phospholipid obtained by substantially removing phosphatidylethanolamine from purified phospholipid, to, for example, the content of not more than about 1 w/w%, may be used. This phospholipid can be obtained by using the phospholipid of egg yolk, soybean and the like and subjecting same to fractionation in organic solvent by a conventional method, and purifying with an inorganic adsorbent such as silica gel, alumina and the like. The thus-obtained phospholipid consists mainly of phosphatidylcholine [[(JP-A-60-149524 (corresponding U.S. Pat. No. 4,684,633, EP-A-150732)]. Alternatively, phosphatidylcholine, phosphatidylethanolamine, phosphatidylserine or phosphatidylinositol itself can be used. The dispersing medium may be water and the like, with preference given to purified water. This $PGE_1$ precursor-containing lipid emulsion mainly comprises a vegetable oil (5–50% w/v), phospholipid (1–300, preferably 5–100, more preferably 10–50, parts by weight, compared with 100 parts by weight of the vegetable oil), and a suitable amount of water.

The PGE$_1$ precursor-containing lipid emulsion according to the present invention can contain, in addition to the above-mentioned ingredients, emulsifier, preservative, stabilizer, high molecular weight substance, isotonizing agent and the like, where necessary.

The emulsifier is exemplified by a fatty acid having 6 to 22, preferably 12 to 20, carbon atoms, a pharmacologically acceptable salt thereof, an aliphatic amine having 2 to 22 carbon atoms and the like. The fatty acid is free of particular limitation as long as it can be added to a pharmaceutical product, and may be linear or branched. To be specific, linear stearic acid, oleic acid, linoleic acid, palmitic acid, linolenic acid, myristic acid and the like are preferably used. The pharmacologically acceptable salts of these fatty acids may be, for example, alkali metal salt (e.g., sodium salt, potassium salt and the like), alkaline earth metal salt (e.g., calcium salt, magnesium salt and the like) and the like. Moreover, the aliphatic amine is free of particular limitation as long as it can be added to a pharmaceutical product and may be linear or branched primary amine having 2 to 22 carbon atoms, secondary amine having 2 to 22 carbon atoms, and the like. Specifically, ethanolamine, propylamine, octylamine, stearylamine, oleylamine and the like can be used. The content of the emulsifier when it is a fatty acid or a salt thereof is preferably not more than 0.3% (w/v). When it is an aliphatic amine and the like, the content is preferably not more than 0.1% (w/v).

The stabilizer is free of particular limitation as long as it can be used for pharmaceuticals, and may be cholesterol, phosphatidic acid and the like. The content thereof when it is cholesterol is preferably not more than 0.5% (w/v), more preferably not more than 0.1% (w/v). When it is phosphatidic acid, the content is preferably not more than 5% (w/v), more preferably not more than 1% (w/v).

The high molecular weight substance is free of particular limitation as long as it can be used for pharmaceuticals, and may be albumin, dextran, vinyl polymer, non-ionic surfactant, gelatin, hydroxyethyl starch and the like. The albumin is originated from human to avoid the problems of antigenicity and the like. The vinyl polymer may be polyvinylpyrrolidone and the like. The non-ionic surfactant may be polyalkylene glycol, (e.g., polyethylene glycol having an average molecular weight of 1,000–10,000, preferably 4,000–6,000 and the like), polyoxyalkylene copolymer (e.g., polyoxyethylene-polyoxypropylene copolymer having an average molecular weight of 1,000–20,000, preferably 6,000–10,000 and the like), hydrogenated castor oil polyoxyalkylene derivative [e.g., hydrogenated castor oil polyoxyethylene-(20)-ether, hydrogenated castor oil polyoxyethylene-(40)-ether, hydrogenated castor oil polyoxyethylene-(100)-ether and the like], castor oil polyoxyalkylene derivative [e.g., castor oil polyoxyethylene-(20)-ether, castor oil polyoxyethylene-(40)-ether, castor oil polyoxyethylene-(100)-ether and the like] and the like. The content thereof when it is a high molecular weight substance is preferably 10–500 parts by weight, more preferably 50–100 parts by weight, per 100 parts by weight of the PGE$_1$ precursor.

The isotonizing agent may be glycerol, glucose and the like.

The amount of the PGE$_1$ precursor to be added to the above-mentioned lipid emulsion can be varied according to the form and use of the emulsion. In general, an extremely trace amount thereof in the emulsion (e.g., about 0.1–100 µg/ml) is sufficient.

A particularly preferable composition of the PGE$_1$ precursor-containing lipid emulsion may be as follows.

| | |
|---|---|
| PGE$_1$ precursor | 1–100 µg |
| purified soy bean oil | 50–500 mg |
| highly purified lecithine | 5–50 mg |
| oleic acid | 0.1–5 mg |
| con. glycerol | 5–50 mg |
| distilled water | appropriate amount |
| Total | 1 ml |

The PGE$_1$ precursor-containing lipid emulsion can be prepared by various methods without particular limitation. Basically, it is prepared by adding water as a dispersing medium, particularly purified water, to an oily liquid consisting of a PGE$_1$ precursor and a different oil component and emulsifying by a suitable method to make same homogeneous. To be specific, the following method and the like can be used. That is, a given amount of a PGE$_1$ precursor, an oil component (preferably soybean oil), phospholipid, and, where necessary, the aforementioned additives and the like are mixed and heated to give a solution, and the solution is homogenized in a conventional homogenizer (e.g., high pressure jet type homogenizer, ultrasonic homogenizer and the like) to give a water-in-oil type dispersion. Then, a necessary amount of water is added, the mixture is again homogenized in the above-mentioned homogenizer to convert same to an oil-in-water type emulsion. An additive such as a stabilizer, an isotonizing agent and the like may be added after preparing a lipid emulsion for easy preparation [JP-A-58-222014 (corresponding USP 4493847, EP-A-97481)].

Following the above-mentioned treatment, sterilization or eradication treatment may be applied. The sterilization treatment may be conventional, such as sterilization by filtration, γ-ray irradiation, high pressure heat treatment and the like.

The PGE$_1$ precursor-containing lipid emulsion thus prepared can be used as the promoter of the present invention as it is or, where desired, upon addition of other ingredients. Examples of other ingredients include eicosapentaenoic acid (so-called EPA), docosahexaenoic acid (so-called DHA) and the like. The lipid emulsion preferably has an average particle size of not more than 1 µm, more preferably 0.2–0.4 µm.

The following explains the case where a preparation having the form other than lipid emulsion is obtained using this PGE$_1$ precursor.

For inclusion in cyclodextrin (CD), for example, a PGE$_1$ precursor is dissolved in a solvent (ethanol and the like), a solution of cyclodextrin dissolved in water and the like with heating is added thereto, the resulting solution is cooled to allow precipitation, and the precipitate is filtered and dried under reduced pressure.

Preparation of a liposome includes the steps of, for example, dissolving a phospholipid in a solvent (chloroform and the like), adding a solution of PGE$_1$ precursor in a solvent (ethanol and the like) thereto, evaporating the solvent, adding a phosphate buffer thereto, shaking, ultrasonicating and centrifuging, and filtering the supernatant through a membrane filter and the like.

An ethanol solution can be prepared by dissolving a PGE$_1$ precursor in ethanol. This ethanol solution is diluted with physiological saline, glucose solution and the like when in use.

The above-mentioned lipid emulsion and other preparations can be adjusted in pH, salt concentration, osmotic pressure and the like by conventional methods. Where necessary, they can be made into a lyophilized preparation.

In the promoter of the present invention, the $PGE_1$ precursor itself has not only an angiogenesis promoting effect but an effect of potentiating angiogenesis by a growth factor.

The angiogenesis promoter of the present invention can be administered parenterally in the form of an injection etc., with preference given to intravenous injection. The dose thereof is preferably 1–1000 μg/day as a $PGE_1$ precursor, which is preferably administered by sustained intravenous injection at 0.01–1000 ng/kg/min once a day.

The angiogenesis promoter of the present invention can potentiate the angiogenic effect of a drug known to have an angiogenic effect by concurrently using the drug. In this case, the angiogenesis promoter of the present invention and the drug having an angiogenic effect may be administered in such a manner that they exist in a living body during the same period of time. They may be prepared into a single pharmaceutical preparation or separately into individual preparations. When they are separate preparations, the administration route and dose may be the same or different.

The known drug having an angiogenic effect is exemplified by a growth factor, heparin, adenosine, dipyridamole and the like. The growth factor is exemplified by b-FGF, TGF (transforming growth factor) β, VEGF (vascular endothelial growth factor), HGF (hepatocyte growth factor), EGF (epidermal cell growth factor) and the like. The method of use and dose of these are free of limitation as long as they are within the known ranges.

EXAMPLES•EXPERIMENTAL EXAMPLES

Figure 1:
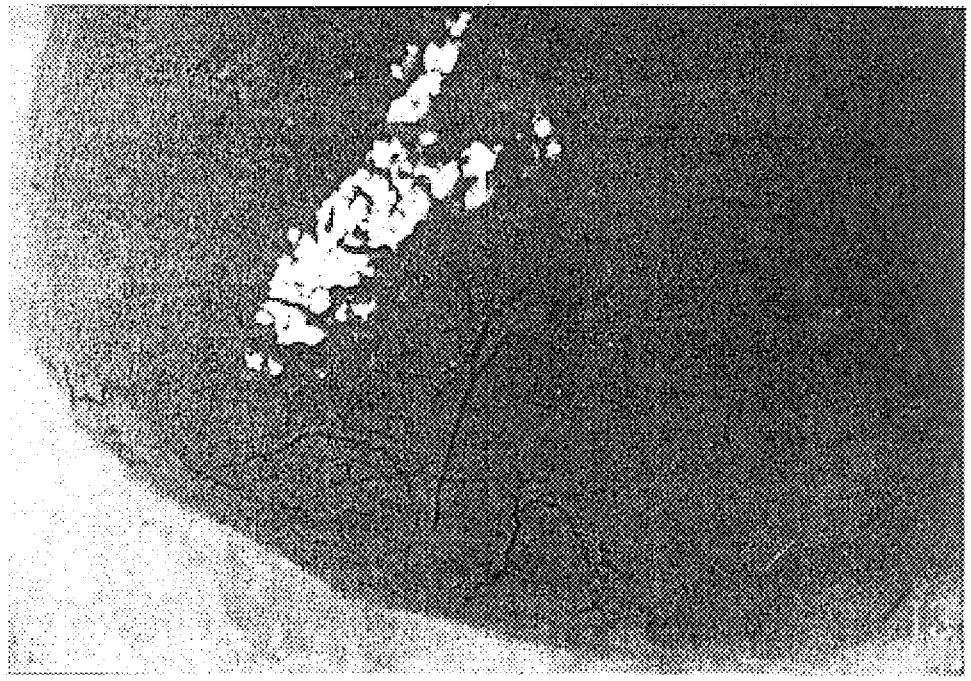
FIG. 1 shows the results of angiogenesis of the vehicle administration group in Experimental Example 1.

The present invention is explained in detail in the following Examples and Experimental Examples. The invention is not limited by these Examples in any way.

Example 1
Inclusion in CD

To a solution of butyl 9-butyryloxy-11α,15S-dihydroxyprosta-8,13E-dien-1-oate (hereinafter to be referred to as AS, 17 mg) in ethanol (0.2 ml) was added a solution of β-cyclodextrin (257 mg) in water (6 ml) prepared by dissolving with warming. The mixture was warmed to 45° C. for dissolution and cooled to room temperature to allow precipitation. The precipitate was left standing at 0° C. overnight and filtered. After washing with 50% aqueous ethanol solution, the residue was dried under reduced pressure to give a cyclodextrin (CD) inclusion compound.

Example 2
Formation of Liposome

Egg yolk phosphatidylcholine (60 mg) and oleylamine (11 mg) were dissolved in chloroform (5 ml), and AS (30 μg) dissolved in ethanol (100 μl) was added. The mixture was placed in an eggplant flask and the solvent was evaporated by rotary evaporator. Thereto was added 0.1 M isotonic phosphate buffer (1 ml, pH 5) and the mixture was subjected to shaking, ultrasonication and centrifugation. The supernatant was passed through a 0.2 μm membrane filter to give a liposome preparation.

Example 3
Formation of Ethanol Solution

AS (500 μg) was dissolved in ethanol (1 ml) to give an ethanol solution. This is used upon dilution in physiological saline, glucose solution and the like when in use.

Example 4
Formation of Lipid Emulsion

To purified soybean oil (30 g) were added purified egg yolk phospholipid (5.4 g), AS (1.5 mg) and oleic acid (0.72 g) and the mixture was heated at 40–75° C. for dissolution. Thereto were added distilled water (200 ml) and then Japan Pharmacopoeia glycerol (7.5 g). Distilled water at 20–40° C. for injection was added to make the total amount 300 ml and the mixture was crudely emulsified in a homogenizer. This was passed 10 times under pressurization (first time 120 $kg/cm^2$, the total 500 $kg/cm^2$) in a Manton-Gaulin homogenizer for emulsification to give a homogenized extremely fine lipid emulsion containing $PGE_1$ precursor. This emulsion had an average particle size of 0.2–0.4 μm, and did not contain particles having a particles size of not less than 1 μm.

Experimental Example 1

Using the promoter of the present invention, the angiogenic effect was evaluated.

(1) Preparation Used

As the promoter of the present invention, the AS-containing lipid emulsion of Example 4 was diluted with a 10% lipid emulsion (Intralipos®, manufactured by the Green Cross Corporation, produced and sold by Yoshitomi Pharmaceutical Industries, Ltd. since April 1, 1998) and used. For the vehicle administration control group, the above-mentioned 10% lipid emulsion alone was used.

(2) Experimental Method

Rats were anesthetized and the dorsal median line was incised for about 1 cm and an air pocket was made subcutaneously at about 2.5 cm toward the tail side with a Kocher clamp. A hemostatic gelatin sponge (Spongel®, 1.0×1.0×0.5 cm; manufactured by Yamanouchi Pharmaceutical Co., Ltd.) infiltrated with physiological saline was implanted therein to prepare rat sponge models.

The incisive region was sutured, antisepticized and intramulscular injection of an antibiotic was given, after which the rats were returned to the breeding cages. Each preparation was bolus administered via the tail vein once a day from the day of sponge implanting to day 4. After 4 days from the implanting, 8 rats per group were sacrificed. The back was opened, and the surrounding tissue was removed trying not to damage the implanted sponge and the surface of the sponge was photographed. All the sponges were taken out and a 0.1M aqueous ammonia (2 ml) was added. The sponges were stood for 4 hr to extract hemoglobin in the sponge. Hemoglobin in the extract (100 μl) was quantitated using an assay kit (hemoglobin B-TESTWAKO; manufactured by Wako Pure Chemical Industries, Ltd.). The amount of the hemoglobin in the sponge was calculated and used as the index of angiogenesis.

(3) Statistical Processing

For the evaluation of the angiogenic effect, a multiple comparison test by Dunnett method was performed to examine significant difference, using the vehicle administration group as a control. The significance was ascribed at less than 5% risk rate.

(4) Results
i) Hemoglobin Content of Sponge (Table 1)

When AS (3 μg/kg) was intravenously bolus-administered in a consecutive manner, AS increased the hemoglobin content compared with the vehicle administration group and a significant difference was observed.

TABLE 1

|  | Hemoglobin in sponge (mg/sponge) at 4 days after implanting |
| --- | --- |
| Vehicle administration group (1 ml/kg) | 1.5 ± 0.9 |
| As administration group (3 μg/kg) | 4.4 ± 0.8* |

The numerals in the Table show mean ± standard error.
*P < 0.05 compared with vehicle administration group (Dunnett method)

ii) Observation of Photograph

Figure 2:
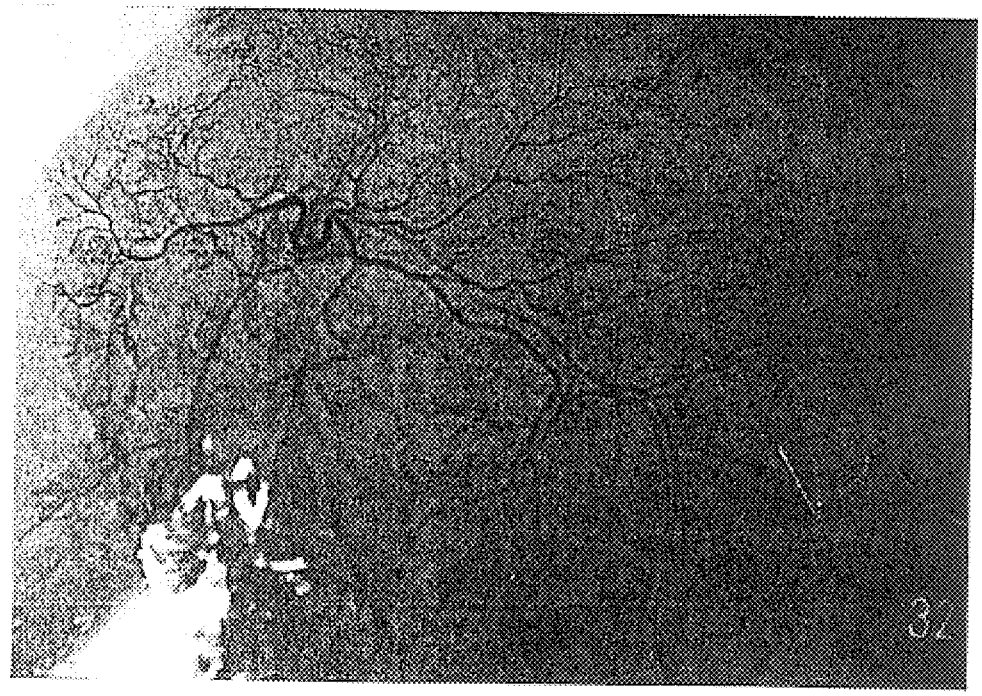
FIG. 2 shows the results of the AS administration group in Experimental Example 1.

In the vehicle administration group (FIG. 1), a few neovascularized blood vessels were observed on the surface of the sponge. In the AS administration group (FIG. 2), a noticeable blood vessel network that allows visual observation was found, showing superior angiogenesis.

iii) Summary

When AS was administered, a noticeable blood vessel network was observed, demonstrating a significant increase in the hemoglobin content of the sponge as compared with the vehicle administration group. Therefore, it was confirmed that AS promoted angiogenesis.

Experimental Example 2

Using the promoter of the present invention, the promoting effect on the angiogenesis by b-FGF was evaluated.

(1) Preparation Used

In the same manner as in Experimental Example 1, as the promoter of the present invention, the AS-containing lipid emulsion of Example 4 was diluted with a 10% lipid emulsion (Intralipos®, manufactured by the Green Cross Corporation, produced and sold by Yoshitomi Pharmaceutical Industries, Ltd. since Apr. 1, 1998) and used. For the vehicle administration control group, the above-mentioned 10% lipid emulsion alone was used.

(2) Experimental Method

Using a hemostatic gelatin sponge infiltrated with physiological saline containing 0.1% BSA (bovine serum albumin) or b-FGF solution (b-FGF 1 mg/ml solution, 100 μl, diluted 10-fold with physiological saline containing 0.1% BSA), and in the same manner as in Experimental Example 1, rat sponge models (6–8 animals per group) were prepared. The vehicle and AS were bolus administered via the tail vein once a day at the volume of 1 ml/kg from the day of sponge implanting to day 4. After 4 days from the implanting, the surface of the sponge was photographed, and the amount of the hemoglobin in the sponge was calculated in the same manner as in Experimental Example 1.

(3) Statistical Processing

For the evaluation of the angiogenic effect, a multiple comparison test (group 1 versus groups 2, 3) by Dunnett method was performed to examine significant difference, using the vehicle alone administration group (BSA-containing physiological saline in sponge +10% lipid emulsion intravenous injection) as a control. For the evaluation of the relationship between AS and b-FGF, an unpaired t-test (group 2 versus group 3) was performed using the b-FGF alone administration group as a control to examine significant difference. The significance was ascribed at less than 5% risk rate.

(4) Results
i) Hemoglobin Content of Sponge (Table 2)

In the b-FGF alone administration group, the hemoglobin content of sponge increased after 4 days from the implanting. On the other hand, in the AS and b-FGF co-administration group, the hemoglobin content of sponge increased significantly as compared with the b-FGF alone administration group.

TABLE 2

| Intravenous injection | In sponge | Hemoglobin in sponge (mg/sponge) at 4 days after implanting | n |
| --- | --- | --- | --- |
| 10% lipid emulsion administration (1 ml/kg) | 0.1% BSA/ physiological saline (100 μl/sponge) | 6.5 ± 0.7 | Group 1 6 |
|  | b-FGF (1 μg/sponge) | 11.8 ± 0.9 | Group 2 8 |
| AS administration (3 μg/kg) | b-FGF (1 μg/sponge) | 20.7 ± 3.1# | Group 3 7 |

The numerals in the Table show mean ± standard error.
P < 0.05 compared with b-FGF alone administration group (unpaired t-test)

ii) Observation of Photograph

Figure 3:
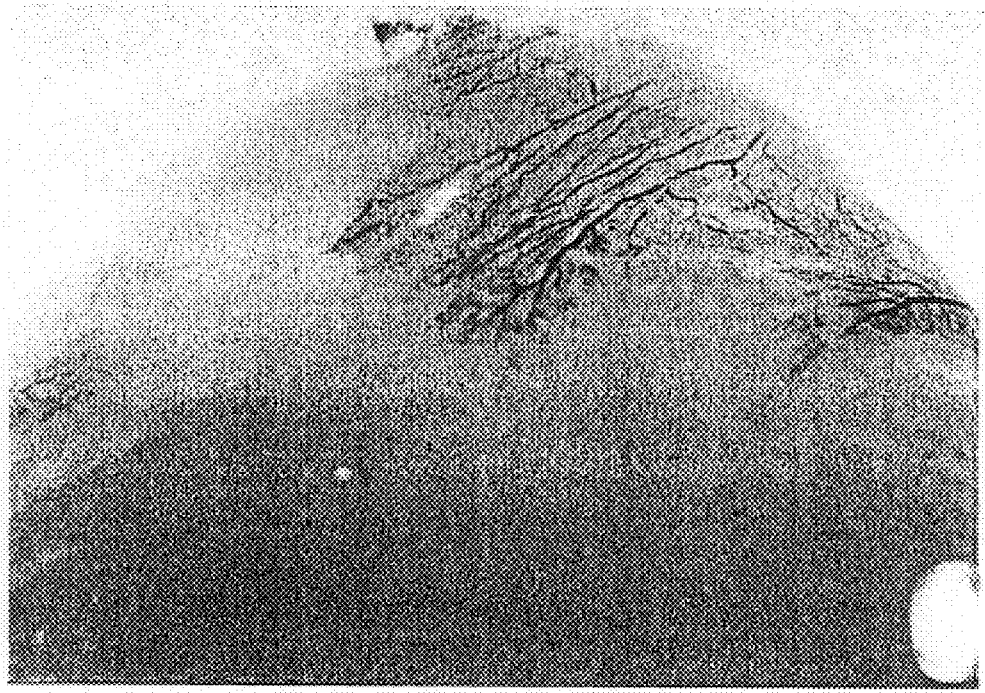
FIG. 3 shows the results of the vehicle alone administration group (group 1) in Experimental Example 2.
Figure 4:
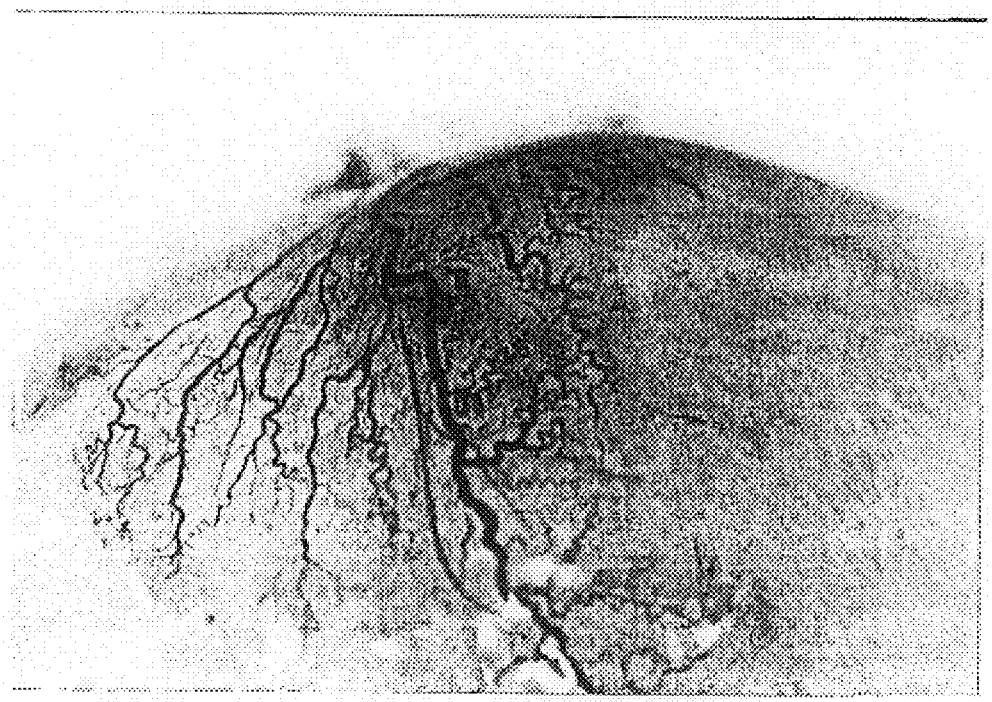
FIG. 4 shows the results of the b-FGF administration group (group 2) in Experimental Example 2.
Figure 5:
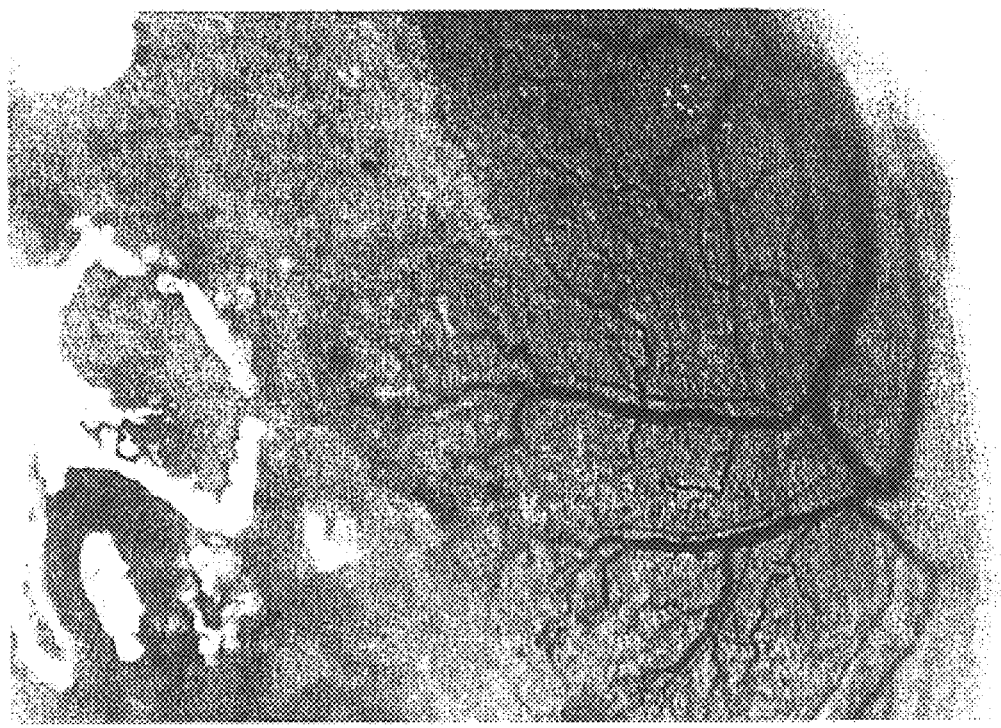
FIG. 5 shows the results of the AS and b-FGF co-administration group (group 3) in Experimental Example 2.

In the vehicle alone administration group (group 1), a few blood vessels were observed on the sponge (FIG. 3). In the b-FGF administration group (group 2), a number of blood vessels were observed on the surface of the sponge, showing formation of a blood vessel network (FIG. 4). In the AS and b-FGF co-administration group (group 3), more noticeable formation of a blood vessel network was observed, with larger blood vessel diameters (FIG. 5).

iii) Summary

When AS and b-FGF were co-administered, the angiogenesis promoting effect by b-FGF was found to be potentiated. Thus, since AS by itself not only shows an angiogenesis promoting effect but potentiates the effect of b-FGF, the angiogenic effect is considered to be expressed more effectively in a site in ischemic tissue or under different disease state, where b-FGF has locally increased, due to the angiogenesis promoting effect of AS.

Experimental Example 3

Toxicity

The lipid emulsion of Example 4 was intravenously administered to the mice, rats and dogs as a $PGE_1$ precursor up to the dose of 250 μg/kg body weight, but no death was found. Serious toxicity was not expressed.

INDUSTRIAL APPLICABILITY

The $PGE_1$ precursor, which is the active ingredient of the promoter of the present invention, itself not only has an angiogenesis promoting effect but also potentiates the angiogenic effect by the drug having said effect, such as b-FGF and the like. Therefore, it can express the angiogenesis promoting effect more effectively in a site in ischemic tissue or under different disease state, where b-FGF has locally increased.

This application is based on a patent application No.231110/1997 filed in Japan, the contents of which are hereby incorporated by reference.

What is claimed is:

1. An angiogenesis promoter rising a compound of the following formula (I)

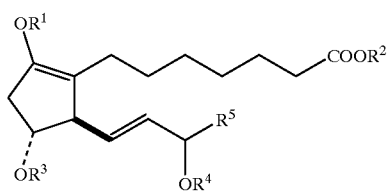

wherein $R^1$ is acyl, $R^2$ is alkyl, $R^3$ and $R^4$ are the same or different and each is hydrogen atom or hydroxy protecting group and $R^5$ is alkyl, as an active ingredient.

2. The angiogenesis promoter of claim 1, wherein $R^1$ is acyl having 2 to 6 carbon atoms, $R^2$ is alkyl having 1 to 30 carbon atoms, $R^3$ and $R^4$ are the same or different and each is hydrogen atom, acyl or aralkyl and $R^5$ is alkyl having 1 to 10 carbon atoms.

3. The angiogenesis promoter of claim 1, wherein $R^1$ is acyl having 2 to 4 carbon atoms, $R^2$ is alkyl having 1 to 4 carbon atoms, $R^3$ and $R^4$ are the same or different and each is hydrogen atom, acetyl, propionyl, benzoyl, benzyl or phenylethyl and $R^5$ is alkyl having 5 to 7 carbon atoms.

4. The angiogenesis promoter of claim 1, wherein the compound of the formula (I) is butyl 9-butyryloxy-11α,15S-dihydroxyprosta-8,13E-dien-1-oate.

5. The angiogenesis promoter of claim 1, which is in the form of a lipid emulsion.

6. A potentiator of an angiogenic effect of a drug having said effect, which comprises the compound of claim 1 as an active ingredient.

7. The potentiator of claim 6, wherein the drug having the angiogenic effect is a growth factor, heparin, adenosine or dipyridamole.

8. The potentiator of claim 7, wherein the growth factor is b-FGF, TGFβ, VEGF, HGF or EGF.

9. A method for potentiating an angiogenic effect of a drug having an angiogenic effect, which comprises administering an effective amount a compound of the following formula (I)

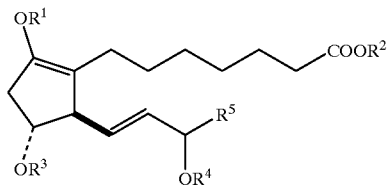

wherein $R^1$ is acyl, $R^2$ is alkyl, $R^3$ and $R^4$ are the same or different and each is hydrogen atom or hydroxy protecting group and $R^5$ is alkyl to a patient in need thereof.

10. A method for promoting angiogenesis, which comprises administering an effective amount of a compound of the following formula (I)

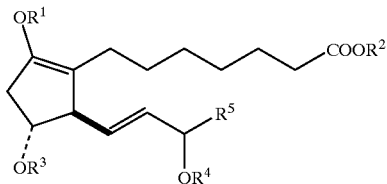

wherein $R^1$ is acyl, $R^2$ is alkyl, $R^3$ and $R^4$ are the same or different and each is hydrogen atom or hydroxy protecting group and $R^5$ is alkyl to a patient in need thereof.

11. The method according to claim 10, wherein $R^1$ is acyl having 2 to 6 carbon atoms, $R^2$ is alkyl having 1 to 30 carbon atoms, $R^3$ and $R^4$ are the same or different and each is hydrogen atom, acyl or aralkyl and $R^5$ is alkyl having 1 to 10 carbon atoms.

12. The method according to claim 10, wherein $R^1$ is acyl having 2 to 4 carbon atoms, $R^2$ is alkyl having 1 to 4 carbon atoms, $R^3$ and $R^4$ are the same or different and each is hydrogen atom, acetyl, propionyl, benzoyl, benzyl or phenylethyl and $R^5$ is alkyl having 5 to 7 carbon atoms.

13. The method according to claim 10, wherein the compound of the formula (I) is butyl 9-butyryloxy-11α,15S-dihydroxyprosta-8,13E-dien-1-oate.

14. A method for producing the angiogenesis promoter according to claim 1, which comprises preparing a lipid emulsion comprising the compound of formula (I).

15. The method according to claim 9, wherein $R^1$ is acyl having 2 to 6 carbon atoms, $R^2$ is alkyl having 1 to 30 carbon atoms, $R^3$ and $R^4$ are the same or different and each is hydrogen atom, acyl or aralkyl and $R^5$ is alkyl having 1 to 10 carbon atoms.

16. The method according to claim 9, wherein $R^1$ is acyl having 2 to 4 carbon atoms, $R^2$ is alkyl having 1 to 4 carbon atoms, $R^3$ and $R^4$ are the same or different and each is hydrogen atom, acetyl, propionyl, benzoyl, benzyl or phenylethyl and $R^5$ is alkyl having 5 to 7 carbon atoms.

17. The method according to claim 9, wherein the compound of the formula (I) is butyl 9-butyryloxy-11α,15S-dihydroxyprosta-8,13E-dien-1-oate.

18. A method for producing the potentiator of an angiogenic effect according to claim 6, which comprises preparing a lipid emulsion comprising the compound of formula (I).

* * * * *